United States Patent
Lentzen et al.

(10) Patent No.: US 9,981,007 B2
(45) Date of Patent: May 29, 2018

(54) DRUG CONTAINING RECOMBINANT MISTLETOE LECTINS FOR TREATING MALIGNANT MELANOMA

(71) Applicant: Cytavis Biopharma GmbH, Hamburg (DE)

(72) Inventors: Hans Lentzen, Rosrath (DE); Klaus Witthohn, Overath (DE)

(73) Assignee: Cytavis Biopharma GmbH, Hamburg (DE)

(*) Notice: Subject to any disclaimer, the term of this patent is extended or adjusted under 35 U.S.C. 154(b) by 0 days. days.

(21) Appl. No.: 15/064,371

(22) Filed: Mar. 8, 2016

(65) Prior Publication Data

US 2016/0175391 A1    Jun. 23, 2016

Related U.S. Application Data

(62) Division of application No. 14/009,961, filed as application No. PCT/EP2012/056479 on Apr. 10, 2012, now abandoned.

(30) Foreign Application Priority Data

Apr. 6, 2011  (EP) ..................... 11161400

(51) Int. Cl.
    *A61K 38/16*    (2006.01)
    *A61K 36/185*   (2006.01)

(52) U.S. Cl.
    CPC .......... *A61K 38/168* (2013.01); *A61K 36/185* (2013.01); *A61K 38/16* (2013.01)

(58) Field of Classification Search
    CPC ..... A61K 36/185; A61K 36/16; A61K 38/168
    USPC ....................................... 514/19.8
    See application file for complete search history.

(56) References Cited

U.S. PATENT DOCUMENTS

| | | | | |
|---|---|---|---|---|
| 6,271,368 | B1 * | 8/2001 | Lentzen ................. | C07K 14/42 424/130.1 |
| 7,635,567 | B2 * | 12/2009 | Muthing ................. | C07K 16/18 435/7.1 |
| 2011/0217232 | A1 | 9/2011 | Muthing et al. | |

FOREIGN PATENT DOCUMENTS

| | | |
|---|---|---|
| DE | 42 21 836 A1 | 1/1994 |
| DE | 197 52 597 A1 | 6/1999 |
| EP | 1 051 495 A2 | 11/2000 |
| WO | WO-03/054544 A2 | 7/2003 |

OTHER PUBLICATIONS

Soler et al, "Complete amino acid sequence of the A chain of mistletoe lectin I," FEBS Letters, 1996, 399: 153-157.*
Thies, A., et al., "Influence of Mistletoe Lectins and Cytokines Induced by them on Cell Proliferation of Human Melanoma Cells in Vitro", Toxicology, 2005, vol. 207, pp. 105-116.
Meyer, S. et al., "Use of Phytopharmaceutical Agents in Dermatology. Indications, Therapeutic Approaches and Side Effects", Der Hautarzt, 2005, vol. 56, No. 1, pp. 483-502.
Mengs, U., et al., "Lektinol, a Standardized Mistletoe Preparation with Antitumoral Activity", Medicinal & Aromatic Plants Abstracts, 2002, vol. 24, No. 1, (1 page).
Thies, A., et al., "Low-Dose Mistletoe Lectin-1 Reduces Melanoma Growth and Spread in a Scid Mouse Xenograft Model", British Journal of Cancer, 2008, vol. 98, No. 1, pp. 106-112.
International Search Report for PCT/EP2012/056479 dated Aug. 29, 2012.

* cited by examiner

*Primary Examiner* — Julie Ha
(74) *Attorney, Agent, or Firm* — Drinker Biddle & Reath LLP

(57) ABSTRACT

A drug and/or pharmaceutical composition comprising recombinant mistletoe lectins for treating metastatic tumors, including malignant melanoma such as stage IV malignant melanoma, and use of said drug, particularly in select patient populations, are described. Recombinant mistletoe lectin polypeptides can be a mistletoe lectin A-chain or fragments thereof. Alternatively, the recombinant mistletoe lectin polypeptides can be mistletoe lectin B-chain or fragments thereof. The drug can be used for the treatment of stages III and IV of a metastatic tumor or skin cancer, as well as to treat non-responders and therapeutic failures of a standard tumor therapy. The drug can be used in a dosage in a range of 3-7 ng recombinant mistletoe lectin per kg body weight. The dosage of the recombinant mistletoe lectin can also be 200-500 ng, independently of body weight. The drug can be administered once a week, or more frequently.

10 Claims, 1 Drawing Sheet

Survival curve according to Kaplan-Meier (x-axis: days, y-axis: survival time of the entire patient population)
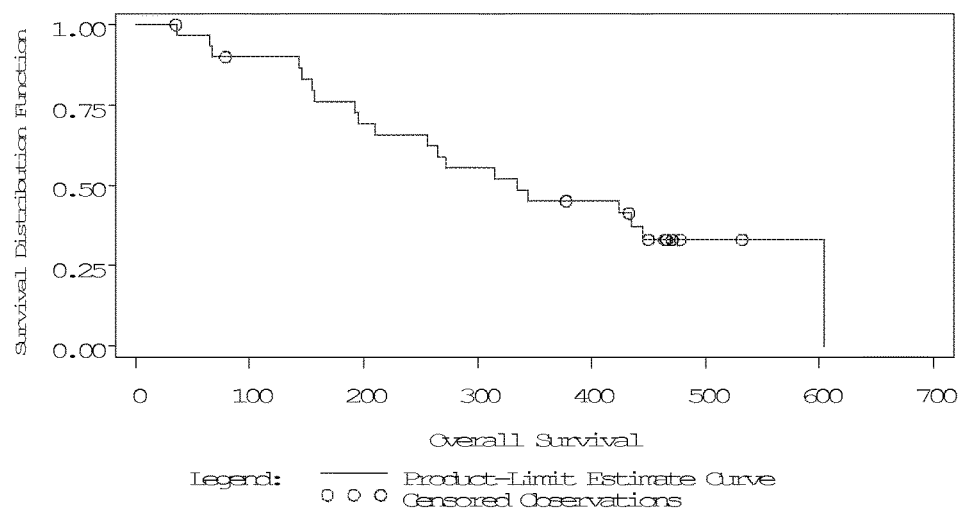

SEQUENCE LISTING

<160> NUMBER OF SEQ ID NOS: 12

<210> SEQ ID NO 1
<211> LENGTH: 253
<212> TYPE: PRT
<213> ORGANISM: Artificial sequence -continued
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (5)..(5)
<223> OTHER INFORMATION: Xaa can be Ile or Leu
<220> FEATURE:
<221> NAME/KEY: misc_feature
<222> LOCATION: (16)..(16)
<223> OTHER INFORMATION: Xaa can be Glu or Asp

<400> SEQUENCE: 1

Xaa Tyr Glu Arg Xaa Arg Leu Arg Val Thr His Gln Thr Thr Gly Xaa
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
        35                  40                  45

Ser Asp Ala Gln Arg Phe Val Leu Val Glu Leu Thr Asn Gln Gly Gly
    50                  55                  60

Asp Ser Ile Thr Ala Ala Ile Asp Val Thr Asn Leu Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Ser Ser Leu Pro Phe
            100                 105                 110

Asn Gly Ser Tyr Pro Asp Leu Glu Arg Tyr Ala Gly His Arg Asp Gln
        115                 120                 125

Ile Pro Leu Gly Ile Asp Gln Leu Ile Gln Ser Val Thr Ala Leu Arg
    130                 135                 140

Phe Pro Gly Gly Ser Thr Arg Thr Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Ala Arg Gln Tyr Ile Asn Ser Gly Ala Ser Phe Leu Pro Asp Val Tyr
            180                 185                 190

Met Leu Glu Leu Glu Thr Ser Trp Gly Gln Gln Ser Thr Gln Val Gln
        195                 200                 205

His Ser Thr Asp Gly Val Phe Asn Asn Pro Ile Arg Leu Ala Ile Pro
    210                 215                 220

Pro Gly Asn Phe Val Thr Leu Thr Asn Val Arg Asp Val Ile Ala Ser
225                 230                 235                 240

Leu Ala Ile Met Leu Phe Val Cys Gly Glu Arg Pro Ser
                245                 250

<210> SEQ ID NO 2
<211> LENGTH: 256
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (16)..(16)

```
<223> OTHER INFORMATION: Xaa can be Asp or Glu
<220> FEATURE:
<221> NAME/KEY: misc_feature
<222> LOCATION: (64)..(64)
<223> OTHER INFORMATION: Xaa can be Gly or Gln
<220> FEATURE:
<221> NAME/KEY: misc_feature
<222> LOCATION: (67)..(67)
<223> OTHER INFORMATION: Xaa can be Ile or Val
<220> FEATURE:
<221> NAME/KEY: misc_feature
<222> LOCATION: (76)..(76)
<223> OTHER INFORMATION: Xaa can be Leu or Ala
<220> FEATURE:
<221> NAME/KEY: misc_feature
<222> LOCATION: (108)..(108)
<223> OTHER INFORMATION: Xaa can be Asp-Arg or can be deleted
<220> FEATURE:
<221> NAME/KEY: misc_feature
<222> LOCATION: (114)..(114)
<223> OTHER INFORMATION: Xaa can be Asn or Thr
<220> FEATURE:
<221> NAME/KEY: misc_feature
<222> LOCATION: (118)..(118)
<223> OTHER INFORMATION: Xaa can be Pro or Thr
<220> FEATURE:
<221> NAME/KEY: misc_feature
<222> LOCATION: (135)..(135)
<223> OTHER INFORMATION: Xaa can be Asp or Glu
<220> FEATURE:
<221> NAME/KEY: misc_feature
<222> LOCATION: (142)..(142)
<223> OTHER INFORMATION: Xaa can be Ser or Thr
<220> FEATURE:
<221> NAME/KEY: misc_feature
<222> LOCATION: (146)..(146)
<223> OTHER INFORMATION: Xaa can be Phe or Tyr
<220> FEATURE:
<221> NAME/KEY: misc_feature
<222> LOCATION: (153)..(153)
<223> OTHER INFORMATION: Xaa can be Ala or Thr
<220> FEATURE:
<221> NAME/KEY: misc_feature
<222> LOCATION: (178)..(178)
<223> OTHER INFORMATION: Xaa can be Ala or Tyr
<220> FEATURE:
<221> NAME/KEY: misc_feature
<222> LOCATION: (181)..(181)
<223> OTHER INFORMATION: Xaa can be Tyr or Asp
<220> FEATURE:
<221> NAME/KEY: misc_feature
<222> LOCATION: (186)..(186)
<223> OTHER INFORMATION: Xaa can be Ala or Glu
<220> FEATURE:
<221> NAME/KEY: misc_feature
<222> LOCATION: (192)..(192)
<223> OTHER INFORMATION: Xaa can be Val or Met
<220> FEATURE:
<221> NAME/KEY: misc_feature
<222> LOCATION: (220)..(220)
<223> OTHER INFORMATION: Xaa can be Ile or Phe
<220> FEATURE:
<221> NAME/KEY: misc_feature
<222> LOCATION: (225)..(226)
<223> OTHER INFORMATION: Xaa can be Pro-Ser or Pro-Thr
<220> FEATURE:
<221> NAME/KEY: misc_feature
<222> LOCATION: (233)..(233)
<223> OTHER INFORMATION: Xaa can be Thr or Ser
<220> FEATURE:
<221> NAME/KEY: misc_feature
<222> LOCATION: (237)..(237)
<223> OTHER INFORMATION: Xaa can be Asp or Ser
<220> FEATURE:
<221> NAME/KEY: misc_feature
<222> LOCATION: (255)..(256)
<223> OTHER INFORMATION: Xaa can be Ser-Ser or can be deleted

<400> SEQUENCE: 2
```

Xaa Tyr Glu Arg Leu Arg Leu Arg Val Thr His Gln Thr Thr Gly Xaa
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
            35                  40                  45

Ser Asp Ala Gln Arg Phe Val Leu Val Glu Leu Thr Asn Gln Gly Xaa
50                  55                  60

Asp Ser Xaa Thr Ala Ala Ile Asp Val Thr Asn Xaa Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Xaa Ser Ser Leu Pro
                100                 105                 110

Phe Xaa Gly Ser Tyr Xaa Asp Leu Glu Arg Tyr Ala Gly His Arg Asp
            115                 120                 125

Gln Ile Pro Leu Gly Ile Xaa Gln Leu Ile Gln Ser Val Xaa Ala Leu
            130                 135                 140

Arg Xaa Pro Gly Gly Ser Thr Arg Xaa Gln Ala Arg Ser Ile Leu Ile
145                 150                 155                 160

Leu Ile Gln Met Ile Ser Glu Ala Ala Arg Phe Asn Pro Ile Leu Trp
                165                 170                 175

Arg Xaa Arg Gln Xaa Ile Asn Ser Gly Xaa Ser Phe Leu Pro Asp Xaa
            180                 185                 190

Tyr Met Leu Glu Leu Glu Thr Ser Trp Gly Gln Ser Thr Gln Val
            195                 200                 205

Gln His Ser Thr Asp Gly Val Phe Asn Asn Pro Xaa Arg Leu Ala Ile
            210                 215                 220

Xaa Xaa Gly Asn Phe Val Thr Leu Xaa Asn Val Arg Xaa Val Ile Ala
225                 230                 235                 240

Ser Leu Ala Ile Met Leu Phe Val Cys Gly Glu Arg Pro Ser Xaa Xaa
                245                 250                 255

```
<210> SEQ ID NO 3
<211> LENGTH: 257
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 3
```

Xaa Tyr Glu Arg Leu Arg Leu Arg Val Thr His Gln Thr Thr Gly Asp
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
            35                  40                  45

Ser Asp Ala Gln Arg Phe Val Leu Val Glu Leu Thr Asn Gln Gly Gln
            50                  55                  60

Asp Ser Ile Thr Ala Ala Ile Asp Val Thr Asn Ala Tyr Val Val Ala
65                  70                  75                  80

Tyr Gln Ala Gly Asp Gln Ser Tyr Phe Leu Arg Asp Ala Pro Arg Gly

```
                        85                  90                  95
Ala Glu Thr His Leu Phe Thr Gly Thr Thr Arg Asp Arg Ser Ser Leu
                100                 105                 110

Pro Phe Thr Gly Ser Tyr Thr Asp Leu Glu Arg Tyr Ala Gly His Arg
            115                 120                 125

Asp Gln Ile Pro Leu Gly Ile Glu Gln Leu Ile Gln Ser Val Ser Ala
        130                 135                 140

Leu Arg Tyr Pro Gly Gly Ser Thr Arg Ala Gln Ala Arg Ser Ile Leu
145                 150                 155                 160

Ile Leu Ile Gln Met Ile Ser Glu Ala Ala Arg Phe Asn Pro Ile Leu
                165                 170                 175

Trp Arg Tyr Arg Gln Asp Ile Asn Ser Gly Glu Ser Phe Leu Pro Asp
                180                 185                 190

Met Tyr Met Leu Glu Leu Glu Thr Ser Trp Gly Gln Gln Ser Thr Gln
                195                 200                 205

Val Gln His Ser Thr Asp Gly Val Phe Asn Asn Pro Phe Arg Leu Ala
        210                 215                 220

Ile Ser Thr Gly Asn Phe Val Thr Leu Ser Asn Val Arg Ser Val Ile
225                 230                 235                 240

Ala Ser Leu Ala Ile Met Leu Phe Val Cys Gly Glu Arg Pro Ser Ser
                245                 250                 255

Ser

<210> SEQ ID NO 4
<211> LENGTH: 264
<212> TYPE: PRT
<213> ORGANISM: Artificial sequence
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 4

Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Asp Phe Arg Asp
                20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
        50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Leu Trp Gln Ile Trp Gly
                85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
        130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
```

```
                    165                 170                 175

Leu Tyr Gly Asp Gly Ser Ile Arg Pro Lys Gln Asn Gln Asp Gln Cys
                180                 185                 190

Leu Thr Cys Gly Arg Asp Ser Val Ser Thr Val Ile Asn Ile Val Ser
            195                 200                 205

Cys Ser Ala Gly Ser Ser Gly Gln Arg Trp Val Phe Thr Asn Glu Gly
        210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro
                260
```

```
<210> SEQ ID NO 5
<211> LENGTH: 268
<212> TYPE: PRT
<213> ORGANISM: Artificial sequence
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 5

Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Asp Phe Arg Asp
                20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
        50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Leu Trp Gln Ile Trp Gly
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
        195                 200                 205

Cys Ser Ala Gly Ser Ser Gly Gln Arg Trp Val Phe Thr Asn Glu Gly
    210                 215                 220

Ala Ile Leu Asn Leu Lys Asn Gly Leu Ala Met Asp Val Ala Gln Ala
225                 230                 235                 240
```

-continued

```
Asn Pro Lys Leu Arg Arg Ile Ile Ile Tyr Pro Ala Thr Gly Lys Pro
            245                 250                 255

Asn Gln Met Trp Leu Pro Val Pro Gly Gly Tyr His
            260                 265

<210> SEQ ID NO 6
<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (19)..(19)
<223> OTHER INFORMATION: Xaa can be Asn or Ser
<220> FEATURE:
<221> NAME/KEY: misc_feature
<222> LOCATION: (22)..(22)
<223> OTHER INFORMATION: Xaa can be Cys or Arg
<220> FEATURE:
<221> NAME/KEY: misc_feature
<222> LOCATION: (57)..(57)
<223> OTHER INFORMATION: Xaa can be Gly or Asn
<220> FEATURE:
<221> NAME/KEY: misc_feature
<222> LOCATION: (96)..(96)
<223> OTHER INFORMATION: Xaa can be Gly or Asn
<220> FEATURE:
<221> NAME/KEY: misc_feature
<222> LOCATION: (158)..(158)
<223> OTHER INFORMATION: Xaa can be Gly or Gln
<220> FEATURE:
<221> NAME/KEY: misc_feature
<222> LOCATION: (167)..(167)
<223> OTHER INFORMATION: Xaa can be Val or Asp
<220> FEATURE:
<221> NAME/KEY: misc_feature
<222> LOCATION: (171)..(171)
<223> OTHER INFORMATION: Xaa can be Gln or Lys
<220> FEATURE:
<221> NAME/KEY: misc_feature
<222> LOCATION: (174)..(175)
<223> OTHER INFORMATION: Xaa can be Gly or can be deleted or can be
     Gly- Arg or Gly-Lys or Arg or Lys
<220> FEATURE:
<221> NAME/KEY: misc_feature
<222> LOCATION: (196)..(196)
<223> OTHER INFORMATION: Xaa can be Cys or Val or Ser
<220> FEATURE:
<221> NAME/KEY: misc_feature
<222> LOCATION: (212)..(213)
<223> OTHER INFORMATION: Xaa can be Ala-Ala or Ala-Gly or Gly-Ala or
     Gly- Gly
<220> FEATURE:
<221> NAME/KEY: misc_feature
<222> LOCATION: (215)..(216)
<223> OTHER INFORMATION: Xaa can be Ser-Ser or Ser-Gly or Gly-Ser or
     Gly- Gly
<220> FEATURE:
<221> NAME/KEY: misc_feature
<222> LOCATION: (225)..(225)
<223> OTHER INFORMATION: Xaa can be Gly or Tyr
<220> FEATURE:
<221> NAME/KEY: misc_feature
<222> LOCATION: (232)..(236)
<223> OTHER INFORMATION: Xaa232 can be Asn, Ser, Thr or Lys, Xaa233 can
     be Ser or Gly,
     Xaa234 can be Leu or Pro, Xaa235 can be Ala or Met, Xaa 236 can
     be Met or Val
<220> FEATURE:
<221> NAME/KEY: misc_feature
<222> LOCATION: (265)..(265)
<223> OTHER INFORMATION: Xaa can be Pro or Phe
```

<400> SEQUENCE: 6

```
Xaa Asp Asp Val Thr Cys Ser Ala Ser Glu Pro Thr Val Arg Ile Val
1               5                   10                  15

Gly Arg Xaa Gly Met Xaa Val Asp Val Arg Asp Asp Asp Phe His Asp
            20                  25                  30

Gly Asn Gln Ile Gln Leu Trp Pro Ser Lys Ser Asn Asn Asp Pro Asn
                35                  40                  45

Gln Leu Trp Thr Ile Lys Arg Asp Xaa Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Xaa
                85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Xaa Gly Ser
145                 150                 155                 160

Val Trp Val Glu Thr Cys Xaa Ser Ser Gln Xaa Asn Gln Xaa Xaa Trp
                165                 170                 175

Ala Leu Tyr Gly Asp Gly Ser Ile Arg Pro Lys Gln Asn Gln Asp Gln
            180                 185                 190

Cys Leu Thr Xaa Gly Arg Asp Ser Val Ser Thr Val Ile Asn Ile Val
            195                 200                 205

Ser Cys Ser Xaa Xaa Ser Xaa Xaa Gln Arg Trp Val Phe Thr Asn Glu
            210                 215                 220

Xaa Ala Ile Leu Asn Leu Lys Xaa Xaa Xaa Xaa Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Xaa
            260                 265
```

<210> SEQ ID NO 7
<211> LENGTH: 264
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 7

```
Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Asp Phe His Asp
            20                  25                  30

Gly Asn Gln Ile Gln Leu Trp Pro Ser Lys Ser Asn Asn Asp Pro Asn
                35                  40                  45

Gln Leu Trp Thr Ile Lys Arg Asp Gly Thr Ile Arg Ser Asn Gly Ser
    50                  55                  60
```

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Gly
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Gln Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
        195                 200                 205

Cys Ser Ala Gly Ser Ser Gly Gln Arg Trp Val Phe Thr Asn Glu Gly
    210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Tyr Pro Ala Thr Gly Lys Pro
                245                 250                 255

Asn Gln Met Trp Leu Pro Val Pro
            260

<210> SEQ ID NO 8
<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 8

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val

```
            130                 135                 140
Thr Ile Tyr Gly Phe Arg Asp Leu Cys Met Glu Ser Asn Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
                180                 185                 190

Cys Leu Thr Ser Gly Arg Asp Ser Val Ser Thr Val Ile Asn Ile Val
                195                 200                 205

Ser Cys Ser Gly Ala Ser Gly Ser Gln Arg Trp Val Phe Thr Asn Glu
                210                 215                 220

Gly Ala Ile Leu Asn Leu Lys Asn Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
                260                 265

<210> SEQ ID NO 9
<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 9

Xaa Asp Asp Val Thr Cys Ser Ala Ser Glu Pro Thr Val Arg Ile Val
1               5                   10                  15

Gly Arg Ser Gly Met Arg Val Asp Val Arg Asp Asp Phe His Asp
                20                  25                  30

Gly Asn Gln Ile Gln Leu Trp Pro Ser Lys Ser Asn Asn Asp Pro Asn
                35                  40                  45

Gln Leu Trp Thr Ile Lys Arg Asp Asn Thr Ile Arg Ser Asn Gly Ser
                50                  55                  60

Cys Leu Thr Thr Tyr Gly Tyr Thr Ala Gly Val Tyr Val Met Ile Phe
65              70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
                115                 120                 125

Leu Gly Gln Gly Trp Leu Ala Gly Asn Asp Thr Ala Pro Arg Glu Val
                130                 135                 140

Thr Ile Tyr Gly Phe Arg Asp Leu Cys Met Glu Ser Asn Gln Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
                180                 185                 190

Cys Leu Thr Val Gly Arg Asp Ser Val Ser Thr Val Ile Asn Ile Val
                195                 200                 205
```

```
Ser Cys Ser Gly Ala Ser Gly Ser Gln Arg Trp Val Phe Thr Asn Glu
    210                 215                 220

Tyr Ala Ile Leu Asn Leu Lys Ser Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 10
<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 10

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Thr Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 11
```

<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 11

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Lys Gly Pro Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 12
<211> LENGTH: 265
<212> TYPE: PRT
<213> ORGANISM: Artificial sequence
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 12

Xaa Asp Asp Val Thr Cys Ser Ala Ser Glu Pro Thr Val Arg Ile Val
1               5                   10                  15

-continued

```
Gly Arg Asn Gly Met Arg Val Asp Val Arg Asp Asp Asp Phe His Asp
            20              25              30

Gly Asn Gln Ile Gln Leu Trp Pro Ser Lys Ser Asn Asn Asp Pro Asn
            35              40              45

Gln Leu Trp Thr Ile Lys Arg Asp Gly Thr Ile Arg Ser Asn Gly Ser
50                      55                  60

Cys Leu Thr Thr Tyr Gly Tyr Thr Ala Gly Val Tyr Val Met Ile Phe
65                      70              75                  80

Asp Cys Asn Thr Ala Val Arg Glu Ala Thr Ile Trp Gln Ile Trp Asp
            85                  90                  95

Asn Gly Thr Ile Ile Asn Pro Arg Ser Asn Leu Val Leu Ala Ala Ser
            100             105             110

Ser Gly Ile Lys Gly Thr Thr Leu Thr Val Gln Thr Leu Asp Tyr Thr
            115             120             125

Leu Gly Gln Gly Trp Leu Ala Gly Asn Asp Thr Ala Pro Arg Glu Val
130             135             140

Thr Ile Tyr Gly Phe Arg Asp Leu Cys Met Glu Ser Asn Gly Gly Ser
145             150             155             160

Val Trp Val Glu Thr Cys Asp Ser Ser Gln Lys Asn Gln Gly Lys Trp
            165             170             175

Ala Leu Tyr Gly Asp Gly Ser Ile Arg Pro Lys Gln Asn Gln Asp Gln
            180             185             190

Cys Leu Thr Ser Gly Arg Asp Ser Val Ser Thr Val Ile Asn Ile Val
            195             200             205

Ser Cys Ser Gly Ala Ser Gly Ser Gln Arg Trp Val Phe Thr Asn Glu
            210             215             220

Gly Ala Ile Leu Asn Leu Lys Asn Ser Leu Met Val Asp Val Ala Gln
225             230             235             240

Ala Asn Pro Lys Leu Arg Arg Ile Ile Ile Tyr Pro Ala Thr Gly Lys
            245             250             255

Pro Asn Gln Met Trp Leu Pro Val Phe
            260             265
```

DRUG CONTAINING RECOMBINANT MISTLETOE LECTINS FOR TREATING MALIGNANT MELANOMA

CROSS-REFERENCE TO RELATED APPLICATIONS

The application is a divisional application of U.S. Application No. 14/009,961, filed Nov. 1, 2013, the contents of which are incorporated herein by reference in their entirety. U.S. application Ser. No. 14/009,961 is the § 371 National Stage of PCT/EP2012/056479, filed Apr. 10, 2012 which claims the benefit of priority of European application No. 11161400.4, filed Apr. 6, 2011.

SEQUENCE LISTING

The instant application contains a Sequence Listing which has been submitted in ASCII format via EFS-Web and is hereby incorporated by reference in its entirety. Said ASCII copy, created on Mar. 8, 2016 is named 74062_0002_01_SL_ST25.txt and is 33,022 bytes in size.

The invention relates to a drug and/or pharmaceutical composition for treating metastatic tumors, in particular of malignant melanoma, above all of stage IV malignant melanoma, and to the use of said drug, in particular the use of said drug in select patient populations.

Malignant melanoma (also referred to as black skin cancer) is a rapidly and early metastazing tumor of the melanocytes, melanin-producing cells, in the basal cell layer of the epidermis. The extent of the disease is dependent on the extent of the metastasis in the regional lymph nodes and in remote regions of the body. Malignant melanoma is particularly aggressive and pernicious and is responsible for virtually 80% of all deaths due to skin tumors (Parkin D M, Bray F, Ferlay J, Pisani P. 2005. CA Cancer J Clin 55: 74-108). Cases of malignant melanoma are growing at the fastest rate of skin tumors affecting men, and are growing at the second fastest rate of skin tumors affecting women. Worldwide, an incidence of 160,000 new cases and 41,000 deaths each year is assumed (Parkin et al. 2005 (supra)).

For the year 2010, it is expected that 68,000 new cases and 8,700 deaths will occur in the USA (SEER-Statistik, www.seer.cancer.gov), and 62,000 new cases and 16,600 deaths will occur in Europe. In Australia and New Zealand, 10,000 new cases and 1,300 deaths are expected (Parkin et al. 2005 (supra)). It is expected that the seven most significant pharmaceutical markets in the world (USA, Japan, France, Germany, Italy, Spain, Great Britain) will see 138,000 new cases in the year 2010, and approximately 227,000 new cases in the year 2019 (Globocan 2002<http://www-dep.iarc.fr/> [Accessed Apr. 7, 2010], World Population Prospects 2008<http://esa.un.org/unpp/> [Accessed Apr. 7, 2010]).

If malignant melanoma is diagnosed and treated in the early stage, the five-year survival rate is 85%. The survival rate drops dramatically after metastasis (near and distant metastases) of the melanoma. A prospective analysis of eight clinical trials conducted by the Eastern Cooperative Oncology Group (ECOG) with 1362 patients having metastatic malignant melanoma, who were treated with combination chemotherapies, yielded a median survival time of 6.5 months and an assumed five-year survival rate of 6%. Significant parameters for a shortened survival time of patients with metastatic melanoma are a poor general state, visceral metastases, the number of affected organs, and elevated LDH (lactate dehydrogenase) (Manola J, Atkins M, Ibrahim J, Kirkwood J. 2000 J Clin Oncol 18: 3782-93, Balch C M, Gershenwald J E, Soong S-J et al. 2009 J Clin Oncol 27(36): 6199-6206, Korn E L, Liu P-Y, Lee S J et al. 2008 J Clin Oncol 26(4): 527-534).

Metastatic malignant melanoma (so-called stage IV) is typically an incurable disease (Balch et al 2009 (supra)). The current standard therapy for treating patients with stage IV metastatic melanoma is dacarbazine (DTIC) (Garbe C, Hauschild A, Volkenandt M et al. 2005, German guidelines: Malignant Melanoma, www.ado-homepage.de). Dacarbazine is well-tolerated, but offers little advantage to patients in terms of the response rate and survival time. The general use of dacarbazine yields a response rate of 5.3%-23%, although the duration thereof is short (Huncharek M, Caubet J F & McGarry R. 2001 Melanoma Res 11(1): 75-81, Serrone L, Zeuli M & Cognetti F 2000 J Exp Clin Res 19(1): 21-34). A phase III clinical trial yielded no additional evidence that dacarbazine prolongs the survival times of patients. The median survival time after dacarbazine in phase III trials is approximately 7.5 months (Chapman P B, Einhorn L H, Meyers M L et al. 1999 J Clin Oncol 17(9): 2745-2751, Middleton M R, Grab J J, Aaronson N et al. 2000 J Clin Oncol 18(1): 158-166, Atkins M B, Lotze M T, Dutcher J P et al. 1999 J Clin Oncol 17: 2105-2116, Falkson C I, Ibrahim J, Kirkwood J M et al. 1998 J Clin Oncol 16: 1743-1751, Avril M F, Aamdal S, Grob J J et al. 2004 J Clin Oncol 22: 1118-1125, Flaherty L E, Atkins M, Sosman J et al. 2001 J Clin Oncol 19: 3194-3202). Other cytotoxic substances such as temozolomide, which has a response rate (ORR) of 13.5-21%, the substances carboplatin, cisplatin and vindesine (ORR 12-26%) and paclitaxel and fotemustine (ORR 7.4-24.2%) exhibit activity in patients with metastatic melanoma. The clinical efficacy of these therapies is comparable to that of dacarbazine (Chapman et al. 1999 (supra), Middleton et al. 2000 (supra), Atkins et al. 1999 (supra)). For example, the use of treosulfan in a second-line therapy after dacarbazine resulted in a median survival time of 6.5 months and a one-year survival rate of 33.9%, combined with 15-18% serious hematological side effects (Neuber K, Reinhold U, Deutschmann A et al 2003 Melanoma Res 13: 81-85).

Many of these substances are used in combination therapies (polychemotherapy) with the objective of increasing the response rates and prolonging the survival time of the patients. Although polychemotherapies increased the response rate, the therapy did not affect the survival rate (OS) in comparison with the general use of dacarbazine (Agarwala S S, Glaspy J, O'Day S J et al. 2002 J Clin Oncol 20: 125-133, Eton 0, Legha S S, Bedikian A Y et al. 2002 J Clin Oncol 20: 2045-2052, Falkson et al 1998 (supra), Avril et al. 2004 (supra)). Two examples of polychemotherapies are the BHD regime (ORR: 12.7%-30.4%) and the DVP regime (ORR: 31.4%-45%).

In addition to chemotherapy, an immunotherapy with high-dose interleukin-2 (IL-2), which is approved for this therapy, has been used for a few years in patients with metastatic malignant melanoma. Reports of significant clinical effects are known, although select patient groups are affected (Danson S, Lorigan P, Arance A et al. 2003 J Clin Oncol 21: 2551-2557). The tumor response rates that were achieved (ORR: 16%-21.5%) are accompanied by extensive multiple organ toxicities, however, and therefore limit the use of IL-2. Similar results are obtained with the use of a high dosage and a moderate dosage of interferon-alpha (IFN-alpha). Treatment with GM-CSF appeared to be successful only in small studies and in clinical trials of the early phase.

The combination of chemotherapy drugs and cytokines (polychemoimmunotherapy) shows partially highly response rates (ORR) in comparison to monotherapies, but the survival time is not improved. For example, the combination of IL-2 and cisplatin exhibited a high response rate, of 50%, having a short duration, although this was accompanied by strong side effects (undesired effects). In a comparison of a monotherapy with dacarbazine and a combination of dacarbazine, cisplatin, IFN- and IL-2, no differences were observed between the two methods of treatment (Flaherty et al. 2001 (supra), Danson et al. 2003 (supra), Agarwala et al. 2002 (supra), Eton et al 2002 (supra), Falkson et al 1998 (supra)). A combination of chemotherapy (cisplatin, vinblastine, dacarbazine) combined with a long-term application of biotherapeutic agents (interleukin-2, interferon alfa-2b and GM-CSF in various regimens) resulted in a median survival time of 14 months for patients with metastatic malignant melanoma. This prolongation of the general survival time was accompanied by a large number of hematological and non-hematological side effects having CTC grade 3 and CTC grade 4. (O'Day S J, Atkins M B, Boasberg P et al. 2009 J Clin Oncol 27(36): 6207-6212).

In terms of metastatic tumors, the study results for Ipilimumab (BMS, Yervoy®), a monoclonal antibody that detects human CTLA-4, are successful. The median survival time of patients with metastatic melanoma (stage III and stage IV) who were treated with Ipilimumab was significantly prolonged, specifically to 10 months versus 6.4 months in the control group (Hodi F S, O'Day S J, McDermott D F et al. 2010 N Engl J Med 363 (8): 711-723). This corresponds to a one-year survival rate of 45.6% in the Ipilimumab group compared to 25.3% in the control group. The side effects experienced by patients on Ipilimumab were considered to be very serious, however. 10-15% of the patients had serious immunological side effects (CTC grade 3 and grade 4) with effects on the skin and the intestinal tract (Hodi et al. 2010 (supra)).

Therefore, there is a great need to provide drugs that ensure better care or at least significantly increase the life expectancy of patient populations in stage III or stage IV with metastatic tumors, in particular in the event of failure of a standard therapy.

Mistletoe extracts have been used for therapeutic purposes for centuries. Mistletoe preparations have been used with varying degrees of success in cancer therapy in particular (Bocci V 1993 J Biol Regulators and Homeostatic Agents 7(1): 1-6; Gabius H-J, Gabius S, Joshi S S et al. 1993 Planta Med 60: 2-7; Gabius H-J & Gabius S 1994 PZ 139: 9-16; Ganguly C & Das S 1994 Chemotherapy 40: 272-278, Hajto T, Hostanska K, Gabius H_J 1989 Cancer Res 49: 4803-4808, Hajto T, Hostanska K, Frei K et al. 1990 Cancer Res. 50: 3322-3326). It has been shown that the therapeutic effects are attributable to so-called mistletoe lectins (viscumin, Viscum album agglutinin, VAA) in particular. Mistletoe lectins have a cytotoxic effect and induce an unspecific immunostimulation, the positive effects of which are used to treat tumor patients. Various investigations involving mistletoe lectins in vitro (Hajto et al., 1990 (supra); Männel D N, Becker H, Gundt A et al. 1991 Cancer Immunol Immunother 33: 177-182; Beuth J, Ko K L, Tunggal L et al. 1993 Drug Res 43: 166-169) and in vivo (Hajto T 1986 Oncology 43 suppl 1: 51-65; Hajto et al., 1989 (supra), Beuth J, Ko H L, Gabius H-J et al. 1991 In Vivo 5: 29-32; Beuth J, Ko H L, Gabius H-J et al. 1992 J Clin Invest 70: 658-661), and clinical studies (Beuth et al., 1992 (supra)) showed an increased release of inflammmatory cytokines (TNF-alpha, IL-1, IL-6) and an activation of cellular components of the immune system (TH cells, NK cells).

Analysis of mistletoe extract have so far resulted in the identification of three mistletoe lectins (ML-I, ML-II, ML-III) with different molecular weights and sugar-binding specificities. It could be shown that the immunostimulating effect of mistletoe extract is attributable to ML-I. The ML-I lectin consists of two A- and two B-chains (MLA and MLB, respectively), each glycosylated. The A-chain is responsible for an enzymatic inactivation of ribosomes (Endo Y, Tsurugi K & Franz H 1988 FEBS Lett 231: 378-380), while the B-chain participates in carbohydrate binding. The two chains are linked together via disulphide bridges. The resulting mistletoe lectin monomers can associate into dimers with the formation of non-covalent bonds.

It is also possible to produce the biologically active mistletoe lectin using recombinant technology. EP 0751221 describes the isolation of mistletoe lectin polypeptides as a structurally homogeneous substance, wherein, proceeding from the genetic sequences of mistletoe lectin, recombinant, highly pure single chains (A-chain, B-chain) are produced, which can be reassociated in vitro and thereby yield a recombinant mistletoe lectin holoprotein, which is protein-chemically, enzymatically and structurally homogeneous, so-called Aviscuminum. According to EP 0751221, the recombinant mistletoe lectin polypeptide is suitable for therapeutic use as a holoprotein, a subchain, and in the form of subfragments, and is covered according to the invention.

Hitherto, recombinant mistletoe lectins were used in the treatment of tumor diseases in particular. However, the use of recombinant mistletoe lectins for the treatment of skin cancer, in particular of malignant melanoma also in the form of a metastatic tumor, is not described in the prior art.

Surprisingly, it has been shown that the survival time of tumor patients with metastatic melanoma (stage III and IV) who are treated with recombinant mistletoe lectins can be prolonged significantly, and the one-year survival rate increases significantly.

The problem addressed by the present invention is that of providing a drug and a pharmaceutical composition, by means of which a metastatic tumor, preferably skin cancer, in particular malignant melanoma, can be effectively treated in animals, mammals and humans.

The problem is solved by providing a drug and a pharmaceutical composition, wherein these contain recombinant mistletoe lectins for the treatment of metastatic tumors, preferably skin cancer, in particular malignant melanoma, wherein the recombinant mistletoe lectins have the following amino acid sequences:

The drug according to the invention preferably comprises the mistletoe lectin A-chain (MLA) and the mistletoe lectin B-chain (MLB), either individually or in combination in either case, also in the form of dimers (see, for example, EP 0 751 221 or EP 1 051 495).

The recombinant mistletoe lectin polypeptide of the mistletoe lectin A-chain comprises the following sequences: SEQ ID No. 1-3, including the isoforms thereof or a functional fragment thereof.

The recombinant mistletoe lectin polypeptide of the mistletoe lectin B-chain comprises the following sequences: SEQ ID No. 4-12, including the isoforms thereof or a functional fragment thereof.

(referred to comprehensively in the following as "recombinant mistletoe lectins")

Further, a recombinant mistletoe lectin according to the invention is preferred, a heterodimer comprising sequences of SEQ ID No. 1 and SEQ ID No. 4; see, for example, EP 0 751 221 (so-called Aviscuminum).

In the context of this invention, the expression "functional fragment" defines fragments of the stated polypeptides that have the same biological function as the polypeptide presented above comprising the particular amino acid sequence.

In this context, the expression "the same biological function" means, for example, that fragments or derivatives of the polypeptides induce the same signals in a cell as the stated peptides. Examples of fragments are peptide domains having defined functions. The "same biological function" also comprises the cytotoxicity, immunostimulation (of the native and the adaptive immune system), stimulation of the release of cytokines, antigenicity, the induction of expression or the activation of surface markers, the induction of apoptosis or endorphin stimulation.

In this case, the expression "biological activity of the recombinant mistletoe lectin" refers to any biological activity from the spectrum of the totality of biological activities of recombinant mistletoe lectin. A function of this type is the pharmacological effect of recombinant mistletoe lectin, for example.

Investigations of ML-I monomers yielded 25 different isoforms, which result from different combinations of various A- and B-chains and different states of glycosylation of the chains.

With respect to the present invention, a mistletoe lectin polypeptide or a fragment thereof that comprises the sequence variability of the various MLA and MLB chains is therefore also considered, according to the invention, for the sequences of SEQ ID No. 1-12.

The drug according to the invention preferably contains a recombinant mistletoe lectin polypeptide comprising sequences of SEQ ID No. 1-12 or a functional fragment thereof, or any combination thereof.

Further, it is preferable for recombinant mistletoe lectins according to the invention to be used in patient populations that do not respond to tumor preparations by means of a standard therapy, or in patient populations that include non-responders or therapeutic failures.

Therefore, the invention also relates to patients or patient populations of non-responders and therapeutic failures having metastatic tumors, in particular malignant melanomas and skin cancer, particularly preferably in stages III and IV, for whom a standard tumor therapy is unsuccessful.

The invention therefore relates to that selection of patients or patient populations who, after an initial treatment of tumors, in particular of malignant melanomas and skin cancer, with a tumor preparation as described above using malignant melanoma as an example, are then treated with the recombinant mistletoe lectins according to the invention. Therefore, those patients or patient populations are preferably treated with the recombinant mistletoe lectins according to the invention who are in the advanced or end stage of a tumor disease, wherein metastasis (stage III and IV), in particular involving malignant melanoma, has occurred. The invention therefore also relates to a combination therapy of a patient, for example to treat malignant melanoma, wherein, firstly, a first anti-tumor preparation, such as dacarbazine, dacarbazine combined with interferon-alpha, dacarbazine combined with vindesine, treosulfan combined with gemcitabine, imatinib is administered, followed by the additional administration of recombinant mistletoe lectins according to the invention exclusively or in combination.

Particularly preferably, the drug according to the invention is suitable for treating malignant melanomas in stage III and IV, since, surprisingly, a significant prolongation of the life of a single patient or a corresponding patient population can be achieved.

This result is completely unexpected, and this special suitability and advantage cannot be expected from a tumor drug per se.

The drug therefore relates to a new anti-tumorigenic preparation for the treatment of metastatic tumors, in particular of malignant melanomas, preferably in stage III and IV.

Within the meaning of this invention, a "malignant melanoma" refers to that which was intially described, wherein stages III and IV describe the forms of malignant melanoma that represent a metastasis of the tumor according to the invention (see, for example, the description in Pschyrembel®, De Gruyter Verlag, Berlin).

The invention also relates to a drug for the treatment of malignant melanoma, which contains the recombinant mistletoe lectin polypeptide, possibly together with a pharmaceutically compatible carrier, with the formation of a pharmaceutical composition. Examples of particularly suitable pharmacologically compatible carriers are known to a person skillled in the art in the field of tumor medical science and comprise buffered sodium chloride solutions, water, inter alia, various types of detergents, sterile solutions, etc. Drugs that comprise such carriers can be formulated using conventional methods. These drugs can be administered to an individual in a suitable dosage. The administration can take place locally, orally, or parenterally, for example, intravenously, intraperitoneally, subcutaneously, intramuscularly, locally, intranasally, intrabronchially or intradermally, or via a catheter at a point in an artery. The type of dosing is determined by the treating physician in accordance with the clinical factors. A person skilled in the art knows that the type of dosing is dependent on various factors, such as the body height and weight, the body surface area, age, gender, or the general health of the patient, and on the preparation to be administered in particular, the duration and type of administration, and on other medications that may be administered in parallel.

The pharmaceutical composition that comprises the recombinant mistletoe polypeptides according to the invention can be administered locally or systemically.

The pharmaceutical composition is used, according to the invention, in the treatment of malignant melanoma.

A dosage of the mistletoe lectins according to the invention for human application of 2-10 ng/kg (body weight) has proven advantageous. The dosage in a range of 3-7 ng/kg is particularly advantageous. The quantity administered is preferably 5 ng/kg body weight. The preferred human dosage that is independent of body weight is 350 ng.

The drug according to the invention is applied over a period of at least 8 weeks at intervals of 1× day up to 1× per week. Preferably, the drug is administered 2 to 3× per week, while 2× per week is particularly preferred.

The invention therefore relates to a method for dosing the recombinant mistletoe lectins according to the invention or the drug according to the invention, wherein the dosage is 2 to 10 ng/kg (body weight). In particular, the invention relates to a method for dosing the recombinant mistletoe lectins according to the invention or the drug according to the invention, wherein the dosage is 200-500 ng, in particular 350 ng, and is administered to the patient at least 1× per week. The patient is preferably a patient in the advanced or end stage of a tumor disease, wherein metastasis (stage III and IV), in particular involving malignant melanoma, has occurred.

The following examples and figures are provided to explain the invention, although the invention is not limited to these examples.

EXAMPLES and FIGURES

Example 1 of a Composition of the Drug

| Solution for injection: 1 mL ampule with 0.5 mL/1.0 mL injection solution | | |
|---|---|---|
| Aviscuminum | 200-500 ng | |
| Sodium monohydrogen phosphate dihydrate | 2.8 mg | 5.6 mg |
| Sodium dihydrogen phosphate dihydrate | 0.078 mg | 0.155 mg |
| Sodium chloride | 3.3 mg | 6.7 mg |
| Polyoxyethylene sorbitan ester (polysorbate) | 0.1 mg | 0.1 mg |
| Glutaminic acid | 0.1 mg | 0.1 mg |
| Water for injection | to make 0.5 ml | to make 1.0 mL |

Example 2 of a Composition of the Drug

| Powder for making a solution for injection, 2R glass vial with | |
|---|---|
| Aviscuminum | 200-500 ng |
| Trehalose | 40.0 mg |
| Sodium chloride | 1.0 mg |
| Tris(hydroxymethyl)aminomethane (TRIS) | 0.6 mg |
| Polyoxyethylene sorbitan ester (polysorbate) | 0.1 mg |
| Hydrochloric acid for adjusting the pH value | |
| for administration, the powder is dissolved in 0.5 mL or 1.0 mL water for injection | |

A clinical study was conducted to investigate whether recombinant mistletoe lectin (Aviscumin, "rML" according to EP 0 751 221) can halt the progression of the disease in patients with stage IV metastatic malignant melanoma after failure of standard therapy, or whether the survival of the patient can be prolonged. The study involved 31 evaluatable patients. Although the progression-free survival was changed, surprisingly, the survival of the patients was significantly increased. The median survival of the patients was 11.0 months, and the one-year survival rate was 45.0%. The prolongation of the survival time was independent of the number of pretreatments and independent of the general condition (ECOG status 0 or 1). The one-year survival rate of a comparable control group, which can be calculated on the basis of the criteria of gender, brain metastases present/not present, the type of metastases (visceral/non-visceral), and general condition (ECOG) according to the data of Korn et al. 2008 (supra), is 33.1%. No side effects occurred over the course of treatment with rML that had a severity of >2 according to the CTC criteria. Therefore, the use of rML is very well tolerated.

TABLE 1

| Demographic data | | | |
|---|---|---|---|
| Patients, n = 31 | | | |
| Sex | n (%) | Male | 16 (51.6) |
| | | female | 15 (48.4) |
| ECOG | n (%) | 0 | 17 (54.8) |
| | | 1 | 14 (45.2) |
| Age (yrs) | Mean | | 65.32 |
| | SD | | 13.53 |
| | Median | | 67.00 |
| Range | | | 20-86 |
| Weight (kg) | Mean | | 76.53 |
| | SD | | 12.42 |
| | Median | | 77.50 |
| Type of melanoma | n (%) | cutaneous | 26 (83.9) |
| | | mucosal | 3 (9.7) |
| | | occult | 1 (3.2) |
| | | other | 1 (3.2) |
| No. of metastatic sites | n (%) | 1 | 13 (41.9) |
| | | 2 | 13 (41.9) |
| | | 3 | 4 (12.9) |
| | | 4 | 1 (3.2) |
| LDH (U/L) at BL | Mean | | 262.71 |
| | SD | | 89.17 |
| | Median | | 245.00 |
| LDH elevation | n (%) | yes | 17 (54.8) |
| | | no | 14 (45.2) |

ECOG = Eastern Cooperative Oncology Group, LDH = Lactate dehydrogenase

Case Study 1:

Patient, female, age: 78 years, stage IV malignant melanoma, ECOG: 1,

Metastases in lymph nodes and lungs, 2 pretreatments with dacarbazine, 15 cycles (420 days) therapy with Aviscuminum (rML) 350 ng, 2×per week, Stabilization of the disease (no tumor growth) for a period of 433 days, survival time: 453 days Case Study 2:

Patient, male, age: 79 years, stage IV malignant melanoma, ECOG: 0, multiple metastases in the liver and lungs, 5 pretreatments with dacarbazine, dacarbazine combined with interferon-alpha, dacarbazine combined with vindesine, treosulfan combined with gemcitabine, imatinib 4 cycles (112 days) therapy with Aviscuminum (rML) 350 ng, 2×per week, Stabilization of the disease (no tumor growth) for a period of 116 days, survival time: 435 days Description of the Figures FIG. 1 describes the survival curve according to the Kaplan-Meier method that was evaluated with respect to the study data.

The invention claimed is:

1. A method of treating a skin cancer comprising administering to a human patient with the skin cancer a drug containing a recombinant mistletoe lectin peptide, the recombinant mistletoe lectin peptide comprising:
   a mistletoe lectin A-chain consisting of the amino acid sequence of SEQ ID NO: 1, or comprises parts and fragments thereof, or is a combination thereof, and
   a mistletoe lectin B-chain consisting of the amino acid sequence of SEQ ID NO: 4, or comprises parts and fragments thereof, or is a combination thereof.

2. The method of claim 1, wherein the method is effective to provide for a median survival of 11 months and a one year survival rate of 45%.

3. The method of claim 1, wherein the method is effective to stop tumor growth for a period of at least 116 days.

4. The method according to claim 1, wherein the skin cancer selected from the group consisting of: a stage III skin cancer, a stage IV skin cancer, and a malignant melanoma.

5. The method according to claim 1, wherein the drug is administered to the human patient in a dosage in a range of 3-7 ng recombinant mistletoe lectin peptide per kg body weight.

6. The method according to claim 5, wherein the drug is administered to the human patient in a dosage of 5 ng recombinant mistletoe lectin peptide per kg body weight.

7. The method according to claim 1, wherein the drug is administered to the human patient in a dosage of 200-500 ng recombinant mistletoe lectin peptide independently of body weight of the human patient.

8. The method according to claim 7, wherein the dosage of the recombinant mistletoe lectin peptide is 350 ng, independently of body weight of the human patient.

9. The method according to claim 1, wherein the drug is administered at least once a week, at least twice a week, or at least three times per week.

10. The method according to claim 1, wherein the human patient is a non-responder or has had a therapeutic failure of a standard tumor therapy.

* * * * *